United States Patent [19]
Richter et al.

[11] 3,961,629
[45] June 8, 1976

[54] USING HYDROPHILIC POLYURETHANE LAPAROTOMY SPONGES

[75] Inventors: Ferdinand Joseph Richter; Charles Teets Riall, both of Danbury, Conn.

[73] Assignee: American Cyanamid Company, Stamford, Conn.

[22] Filed: Feb. 26, 1971

[21] Appl. No.: 119,299

Related U.S. Application Data

[63] Continuation-in-part of Ser. No. 736,181, June 11, 1968, Pat. No. 3,566,871.

[52] U.S. Cl. ............................................. 128/296
[51] Int. Cl.² ........................................ A61F 13/00
[58] Field of Search .................... 128/285, 290, 296

[56] References Cited
UNITED STATES PATENTS

| | | | |
|---|---|---|---|
| 2,884,925 | 5/1959 | Meynier, Jr. | 128/285 X |
| 3,113,568 | 12/1963 | Robins | 128/296 X |
| 3,157,178 | 11/1964 | Benton | 128/296 X |
| 3,190,289 | 6/1965 | Patience | 128/296 |
| 3,324,855 | 6/1967 | Heimlich | 128/296 X |
| 3,368,911 | 2/1968 | Kuntz et al. | 128/296 X |
| 3,371,667 | 3/1968 | Morse | 128/296 X |
| 3,372,696 | 3/1968 | Rudie | 128/296 X |
| 3,566,871 | 3/1971 | Richter et al. | 128/296 |

FOREIGN PATENTS OR APPLICATIONS

| | | | |
|---|---|---|---|
| 229,962 | 8/1960 | Australia | 128/296 |

*Primary Examiner*—Robert W. Michell
*Assistant Examiner*—Henry S. Layton
*Attorney, Agent, or Firm*—Samuel Branch Walker

[57] ABSTRACT

A surgical laparotomy pad having uniquely useful properties comprises a hydrophilic polyurethane sponge in which the sponge pores have a surfactant coating to accelerate absorption of body fluids into the pores at medically desirable rates, the fluids being retained therein by capillarity to affect removal of the fluids from the body. The sponge is flexible, and substantially free from lint, toxicity, and abrasiveness, making it particularly suitable for use in contact with raw living tissue to absorb blood or fluids, and retain tissues temporarily in position during surgical procedures.

1 Claim, 15 Drawing Figures

INVENTORS.
FERDINAND JOSEPH RICHTER
CHARLES TEETS RIALL
BY

*Samuel Branch Walker*

ATTORNEY

INVENTORS.
FERDINAND JOSEPH RICHTER
CHARLES TEETS RIALL
BY

*Samuel Branch Walker*

ATTORNEY

USING HYDROPHILIC POLYURETHANE LAPAROTOMY SPONGES

CROSS REFERENCES

This is a continuation-in-part of copending application Ser. No. 736,181, filed June 11, 1968, now U.S. Pat. No. 3,566,871, Mar. 2, 1971.

BACKGROUND OF THE INVENTION

During surgery, there is frequent need for sponging various portions of the body to remove body fluids such as blood, serum, plasma, lymph, spinal fluid, tissue fluid, urine, sweat, bile juice, and digestive juice. For example, during an initial surgical incision it is common practice to blot the incision and the area adjacent to the incision with sponges to remove blood and other fluids emanating from the incision. After entering the thoracic cavity, abdominal cavity, or other operating field, it is customary to use sponges which have been moistened in saline solution to isolate various organs from the operating field. This is done by packing the organs with sponges to restrain them from entering the operating field and thereby interfering with the operation. The sponges are moistened in saline solution to prevent drying out organs or tissue with which they come into contact.

Sponges are also used in specialized areas of surgery such as ophthalmic surgery, neurosurgery, and spinal surgery, such sponges often having a configuration especially adapted for these particular uses.

GAUZE PAD PRIOR ART

At the present time, gauze pads are the most commonly used medical sponges. These pads are prepared from modified cellulose or rayon and are comprised of multi layers of sheets woven from multi-filament yarns. A radiopaque marker, such as barium sulfate dispersed in a suitable carrier, is usually attached to the pad to assist in locating the pad by X-ray should it be inadvertently left in the body after surgery.

These pads have many disadvantages. Their edges often fray and they tend to shed large amounts of lint. The lint is particularly undersirable. It may pick-up bacteria from non-sterile sections of the operating room and then serve as a carrier of bacteria into the exposed body cavity of the operative patient. Furthermore, the lint particles, upon entering the body cavity, may create undesirable foreign body reaction such as granulomata or adhesions, as discussed in greater detail by Sturdy et al. in Annals of Surgery 165, pgs. 128–134 (1967).

Dry gauze pads may accumulate electrical charges, adding to the explosion hazard in the operating room when anesthetics, such as ether, are being used.

Gauze pads, particularly when dry, are highly abrasive towards sensitive internal body organs. Since these pads are used to sponge these organs and to pack the organs during surgery, the pads are necessarily in intimate contact with the organs and can cause serious trauma to the organs because of their abrasiveness. As the pads absorb blood and other body fluids, they become progressively less pliable and harder, thus tending to continue their undesirable abrasive affect upon organs even after becoming moist. In considering the seriousness of the abrasive character of gauze pads, it should be remembered that the surgeon or his assistant may reposition the pad in the course of an operation, and may frequently remove used pads and insert new ones.

During an operation, the surgeon may desire to cut a pad to a smaller size for a special use. Not only are gauze pads difficult to cut but, after cutting, they tend to fray extensively and to shed lint.

A further disadvantage of the gauze pad is the risk of cross contamination, arising from the common hospital practice of rewashing and reusing the pads several times before they are discarded. After the first laundering, the size of the pad may be reduced as much as 30%. Shrinking continues in subsequent washings, but at a reduced rate. The softness and flexibility progressively diminish during repeated laundering. Before pads can be reused, they must be resterilized as well as rewashed.

This invention envisions elimination of the above disadvantages by providing a novel hydrophilic polyurethane sponge which is eminently suitable for usage in medical applications such as those described hereinabove.

POLYURETHANE SPONGE PRIOR ART

Prior art on hydrophilic or otherwise modified polyurethane foams is voluminous. However, it can be conveniently broken down into four categories.

The first category comprises foams which have been rendered hydrophilic by chemical modification. This is commonly done by adding a hydrophilic agent to the reaction mixture from which the foam is prepared. For example, in U.S. Pat. No. 3,326,823, a hydrophilic polymer is added to a reaction mixture containing a polyisocyanate, a polyether having a monomer of hydrophilic character grafted thereon, and an activator mixture to produce a hydrophilic foam capable of absorbing up to 3.1 grams of water per gram of dry sponge (measured by passing the sponge over the surface of water without pressure), an amount unsuitable for use as a medical sponge wherein water pick up to from 20 to 25 times the dry sponge weight is desirable. U.S. Pat. No. 3,098,048 describes a similar procedure for preparing a sponge containing an ethylene oxide content of 30 to 80 percent. Unfortunately, this sponge foams when wetted to release surfactant over long periods of time; clearly, such a sponge would be unsuitable for medical use, especially within a body cavity.

The second category comprises polyurethane foams which have been impregnated with a hydrophilic agent. For example, U.S. Pat. No. 3,224,889 describes a foam whose pores are coated with fine silica. The sponge is capable of absorbing from 9.5 to 17 grams of water per gram of dry sponge. Were this sponge to be used in surgery, it is possible that silica solids could spill into the body cavity and cause tissue poisoning which could develop into silicosis. Furthermore, this sponge loses wettability when washed in hot or cold water containing fatty acids soaps, thus restricting reuse of the sponges unless special care is taken during laundering. U.S. Pat. No. 3,149,000 describes a polyurethane foam impregnated with polyacrolein. However, acrolein monomer is a known body irritant and the possibility of some monomer being present in the polyacrolein would be a deterrent to the medical usage of the sponge.

The third category comprises polyurethane foams impregnated with various substances for the purpose of releasing the substance from the sponge at a controlled rate upon wetting of the sponge. Generally, the pores of such sponges are substantially filled with impregnant, the pores functioning primarily as a reservoir for the impregnant. Obviously, when the pores of the foam are so filled, any substantial inward flow of fluids such as would be required with a medical sponge, could not be achieved. This third category of polyurethane foam is amply illustrated by U.S. Patent No. 3,088,158 which describes a sponge impregnated with an emulsion suitable for washing and waxing auto finishes upon wetting, and by U.S. Pat. No. 3,262,450 which describes a moistened foam containing a layer of foaming surfactants which, when repeatedly compressed, produces foam for a cleaning purpose. Also included in this category are polyurethane foams impregnated with a germicide and soap solution, having at least one surface sufficiently abrasive for surgical scrubbing so that upon moistening and squeezing the sponge, foam will be produced at the abrasive surface for scrubbing. U.S. Pat. No. 3,002,937 describes a sponge containing zones of fine pore size and zones of much coarser pore size, the sponge containing a detergent. In addition to foaming upon wetting, the size of the large pores (up to ½ inch in diameter) tends to make the sponge excessively abrasive. Furthermore, these large pores, particularly when they appear on the surface of the sponge, will not retain fluids by capillarity when the sponge is disengaged from the environment of the fluid. None of the sponges within this third category would be suitable for medical usage because fluids either are blocked from entering the foam in substantial amounts or because the foam is incapable of retaining sufficiently large amounts of liquids, or because they foam excessively upon wetting.

The fourth category comprises polyurethane foam having an external surface coating of a detergent or disinfectant. Such a product is shown in U.S. Pat. No. 3,283,357 in which the polyurethane foam contains a substantially impermeable outer layer of a germicide-detergent mixture which foams upon wetting. Although the inner pores of the sponge are unfilled, access to these pores is blocked by the continuous impermeable surface layer. As a result, this sponge would be unsuitable for medical use.

U.S. Pat. No. 3,396,419, Richter and Granowitz, DISPOSABLE SURGICAL SCRUB SPONGE AND DISPENSER, shows a multilayer polyurethane sponge, containing sudsing quantities of detergent and an antibacterial agent.

British Pat. No. 1,190,733, Lord, Holmes and Lofts, May 6, 1970 discloses X-ray opaques in sponge structures.

SUMMARY OF THE INVENTION

This invention relates to using novel hydrophilic polyurethane medical sponges whose surfaces are non-abrasive towards exposed internal body organs and which contains at least one zone of pores extending inwardly from a surface of the sponge. The sponge is rendered hydrophilic by a thin coating on the internal surfaces of the pores of at least one surfactant which is a non-flowable liquid at room temperature. It is important that substantially all of the internal pore surfaces be coated with surfactant to insure uniformity of fluid absorption throughout the entire zone of pores. An amount of surfactant is required which accelerates absorption of body fluids into the pores, without compression of the sponge, at a medically preferred rate, while not simultaneously causing any substantial reduction in the volume of the pores so as to interfere with the capacity of the sponge to absorb fluid.

Some polyurethane sponges, particularly those made with a polyester containing hydroxyl groups or carboxy groups which are unreacted, are inherently somewhat hydrophilic, and particularly if treated with a polyhydroxy alcohol retention aid, of the type disclosed in U.S. Pat. No. 2,849,000 for cotton tampons, become hydrophilic, and are useful in the present invention. Hydrophilic Polyurethane Foams are described in U.S. Pat. No. 3,388,081, Merten and Braun, June 11, 1968.

The polyether and polyester urethane foams sold by Tenneco Co. as hydrophilic are in general not adequately hydrophilic for the present use as sold, but if crushed, or texturized, as described in detail below, or treated with a humectant retention aid, of the glycerine type, or both, become more hydrophilic and are a good laparotomy sponge.

Once fluids have entered the pores of the sponge, they are retained therein primarily by capillary action and are thereby conveniently removed from their body environment when the sponge is so removed. The sponge pores must be properly dimensioned to insure said capillary retention of fluid therein.

It is important that the surfactant be non-toxic to the body and also that it not foam when the sponge is wetted with body fluids. It is also important that there be no substantial blockage of access to the pores whereby body fluids are prevented from entering the pores.

The sponges of this invention are conveniently prepared in many different sizes and can be tagged with radiopaque markers, if desired. They can be used in a variety of surgical applications as described hereinbelow. The sponges of this invention are substantially free from toxicity, abrasiveness, and lint; they resist fraying and can be readily cut to any size desired.

Although the sponges are designed for disposibility after being used once, thereby eliminating the risk of cross contamination, they may be washed, resterilized, and reused many times without noticeable shrinkage or diminishment of their hydrophilic properties. Repeated autoclaving of the sponges, for example, enhances their surgical handleability.

Despite the presence of surfactant in the sponges, the sponges are free from a greasy texture. The sponges will rapidly absorb up to about 20 to 25 times their dry weight of fluids. Furthermore, they will absorb such fluids merely by contacting the fluids with the sponge; compression of the sponge is not required to achieve absorption.

It is an object of this invention to provide a novel hydrophilic polyurethane medical sponge which eliminates the numerous disadvantages of the currently used gauze pads as described hereinabove.

DESCRIPTION OF THE PREFERRED EMBODIMENTS

Figure 1:
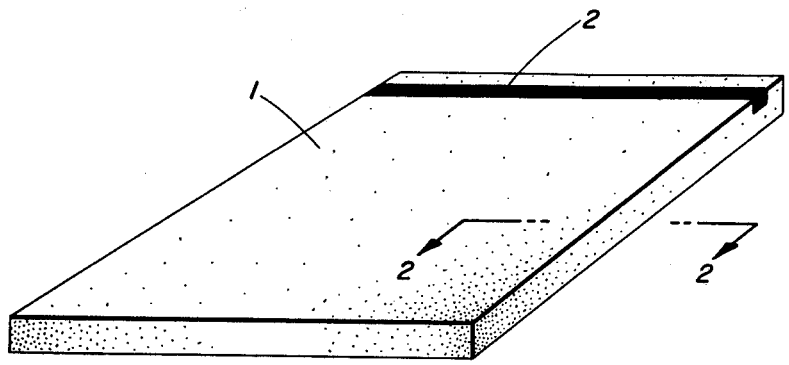
FIG. 1 is a perspective view of a typical disposable polyurethane sponge of this invention, the sponge having a radiopaque tracer attached thereto.

Polyurethane foam suitable for preparing the sponges of this invention may be either the polyester or the polyether type. Polyurethane polyester foams such as those supplied by Scott Paper Company, Chester, Pa., under the names of Scott "Z" or Scott "Q" polyurethane foam, having about 100 pores per inch, said pores being fully reticulated, i.e., open pores, are preferred. A polyurethane polyether foam such as that supplied by Nopco Chemical Co. Newark, N.J., under the name Nopco ST-1840 polyurethane foam, having about 60 to 100 pores per inch, said pores being about 60% reticulated, is also quite suitable. Although reticulated or non-reticulated foam is generally acceptable, 100% reticulated foam is preferred. Reticulated foam may be prepared by a physical or chemical reticulation process. A typical physical reticulation process involves blowing out connecting windows in the foam matrix under high pressure; a typical chemical reticulation process involves removing the connecting windows by treating the foam with a dilute aqueous caustic solution.

The size of the pores of the foam must be sufficiently small to insure retention of fluids therein substantially by capillary action. Foams having from about 40 to about 150 pores per linear inch meet this requirement, with about 100 pores per inch representing a preferred pore density. Should the foam contain less than about 40 pores per inch, the sponge surfaces are too abrasive for medical usage and the pores are too large to retain fluid by capillary action. When foam contains more than 150 pores per inch, pore size becomes too small to permit flow of fluids into the pores at a medically preferred rate.

Since the sponges are frequently used in a bloody surgical field, it is desirable to dye the polyurethane foam a color which will offset the sponges from the surgical field. Blue and green are particularly suitable colors for this purpose and polyurethane foam dyed with these colors is readily available commercially. The dye selected should be non-toxic and generally innocuous toward living tissue.

For medical usage, it is important that the foam be extremely flexible and pliable to permit the surgeon to wrap and contour the foam around various internal organs or to otherwise use the foam to pack such organs with assurance that the foam will stay in place during the operation. To achieve the desired flexibility, coupled with the required foam free volume for adequate absorbency, foam thickness of from 1/32 to ½ of an inch give good results with a thickness of about ⅛ of an inch preferred for many applications.

An acceptable polyurethane foam typically has a void fraction of about 97%; were all the voids to be filled with a fluid such as water, the foam would be capable of retaining about 30 times its dry weight of water.

The sponges can be conveniently cut to a variety of sizes, the size depending on the particular application of the sponge. For example, 4 × 4 and 4 × 8 sponges are particularly suitable for sponging during an initial surgical incision. Larger size sponges are preferred for packing internal organs once the body cavity has been opened and exposed. Sponge sizes suitable for this latter purpose are 4 × 12 inch, 4 × 30 inch, 14 × 14 inch, and 16 × 16; the 4 × 30 inch sponge, for example, is typically rolled into a cylindrical configuration for use in packing body organs. The other sized sponges may be similarly used, or they can be used as is, i.e. without rolling or forming into special configurations.

Sponges suitable for other types of surgery such as ophthalmic and neurosurgery, for example, are of different sizes and configurations as discussed hereinbelow.

FIG. 1 depicts a typical sponge of this invention. Attached to sponge 1 is a radiopaque tracer 2 to permit X-ray detection of the sponge should it be inadvertently left in the body following surgery. A suitable radiopaque tracer is a black polyvinyl chloride filament containing not less than 60% of X-ray grade barium sulfate. This filament is conveniently attached to polyurethane foam by conventional heat sealing techniques whereby the filament is compressed into a ribbon and affixed to the foam as shown in FIG. 1. A tracer material could also be incorporated into the foam during its formation by addition of a suitable amount thereof to the reaction mixture.

The foam is rendered hydrophilic by coating the pore walls of the foam with a thin layer of a surfactant which is a non-flowable liquid at room temperature. Non-flowability eliminates the danger of the surfactant dripping out of the sponge and into the body cavity. The surfactant must be non-toxic to human tissue and, furthermore, must not foam when the sponge is wetted with water, blood, or other body fluids. Surfactants of the anionic, non-ionic, and cationic variety are suitable for imparting the desired hydrophilicity to the polyurethane foam. More particularly, surfactants such as lauryl sulfate (anionic), stearamido propyldimethyl-$\beta$-hydroxyethyl ammonium nitrate (cationic), alkylarly polyethoxylated glycol ethers (nonionic), and polyoxyethylene sorbitan monooleate (nonionic) have been successfully used.

A preferred surfactant is polyoxyethylene sorbitan mono-oleate; this surfactant is sold by Atlas Incorporated, under the trademark of Tween-80. This surfactant is preferred because it is known to be physiologically innocuous and has already been approved by the Federal Food and Drug Administration for internal consumption in such items as food and candy. It has also been approved for use in intravenous and intramuscular pharmaceutical preparations such as those of tetracycline and chlortetracycline. This surfactant is listed under the name Polysorbate 80 in the Merck Index, 7th ed. (1960) at pg. 833 and in the U.S. Pharmacopoeia XV at pg. 566, said publications being incorporated herein by reference.

Two important considerations arise in determining the preferred amount of surfactant. First, sufficient surfactant must be provided to insure accelerating the absorption of body fluids into the sponge, without compression to the sponge, at a medically preferred rate. A "medically preferred rate" exists when there is no undue lag time between contact of the sponge with the fluid and the disappearance of the fluid into the sponge. It is difficult to precisely define such a rate since it varies depending upon the application in which the sponge is being used. For example, when a surgeon desires to have the cutting field cleared of blood during an initial surgical incision, almost instantaneous removal of blood by the sponge is required. On the other hand, when the sponge is inserted into the body cavity for purposes of preventing blood and other body fluids from cascading into the surgical field, instantaneous fluid absorption is not necessarily required provided the rate of absorption is sufficient to prevent the fluids from noticeably obscuring the surgeon's view of the operating field.

The second consideration is that the free volume of the sponge must be maintained at a sufficiently high value to provide a reservoir for a substantial amount of fluid flowing into the sponge. The sponge should have the capability of absorbing at least 20 times its dry weight of water as discussed hereinabove. While increasing the surfactant concentration increases hydrophilicity of the sponge, it tends to decrease the free volume of the sponge by increasing the thickness of surfactant coating on the pore walls. This is best understood by reference to FIG. 2 which is a greatly enlarged cross-sectional view of the foam showing the network of pores 3 within sponge 1 and the thin layer of surfactant coating 4 on the walls of pores 3.

Figure 2:
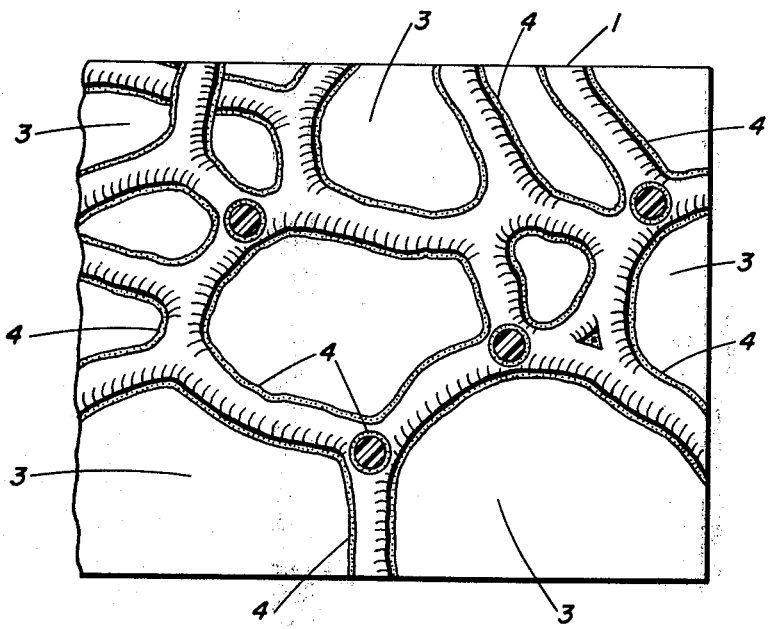
FIG. 2 is an enlarged cross-sectioned view of the sponge taken along plane 2—2 of FIG. 1, and illustrates the nature of the surfactant coating upon the pore walls of the sponge.

The thin continuous surfactant coating shown in FIG. 2 is illustrative only. The nature of the coating can vary provided its function of accelerating absorption of fluids into the sponge is retained. For example, the coating could be a network of fine beads of surfactant resting on the internal pore surfaces; or it could be a continuous or partially continuous thin film of surfactant.

Figure 3:
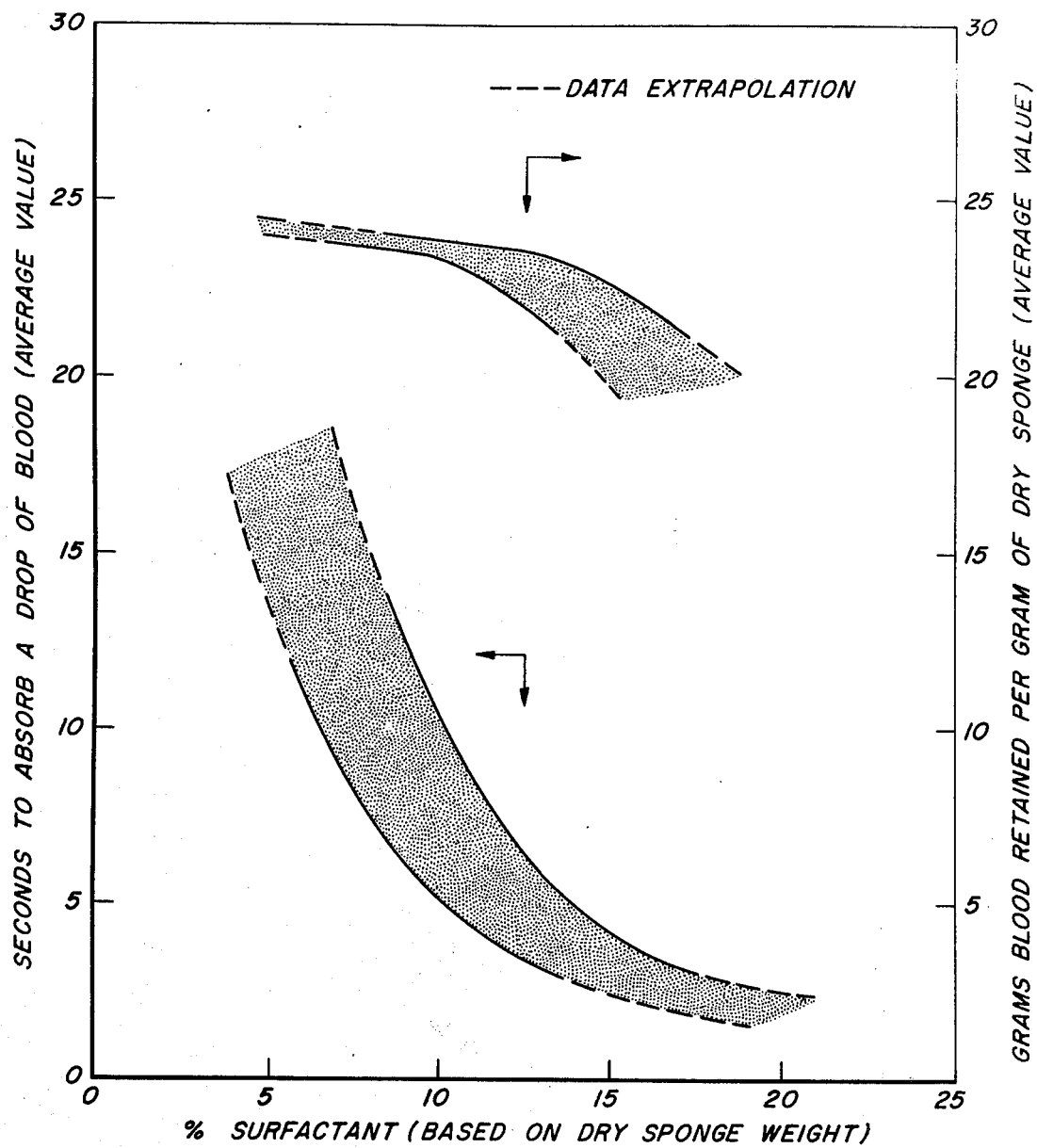
FIG. 3 shows graphically the affect of the surfactant concentration in the sponge upon blood absorption rate and the amount of blood retained per weight of dry sponge.

FIG. 3 shows graphically the effect of surfactant concentration in the sponge upon the average time required to absorb a single drop of blood. FIG. 3 also shows the effect of surfactant concentration in the sponge upon the average quantity of blood retained by the sponge. Generally, a surfactant concentration of from about 0.1% to about 25%, based on dry sponge weight, is operable. Surfactant concentrations below 2%, while acceptable for less demanding medical applications, would not be generally acceptable because of the reduced rate of fluid absorption. Surfactant concentrations above 25% do not noticeably enhance hydrophilicity of the sponge. However, such high surfactant concentrations tend to decrease the quantity of fluid retained by the sponge and, furthermore, tend to impart an undesirable greasy texture to the sponge. A surfactant concentration of about 3 to about 15%, based on the dry weight of the sponge, is quite acceptable with a surfactant concentration of from about 5 to about 10% preferred.

Hygroscopic agents may also be incorporated with the surfactant into the foam, the purpose of such agents being to pick up sufficient moisture from the environment to impart anti-static properties to the foam thereby minimizing any explosion hazard as heretofore discussed.

Generally, any well-known non-toxic drying agent or humectant is suitable, although liquid agents are preferable because they may be readily and uniformly mixed with the liquid surfactant for convenient impregnation into the sponge. Illustrative hygroscopic agents are propylene glycol, diethylene glycol, or other homologs of glycol. A highly preferred hygroscopic agent is U.S.P. grade glycerin since it is known to be non-toxic and readily assimilable by the body. Glycerine is listed in the Merck Index, 7th ed. (1960) at pages 489–490 and in the U.S. Pharmacopoeia XV at pages 309–310, said publications herein incorporated by reference.

The hygroscopic agents have substantially no effect upon hydrophilicity of the sponge. The amount added is not critical; however, sufficient hygroscopic agent must be provided to achieve the desired degree of anti-static behavior while, at the same time, if an excessive amount of hygroscopic agent is added, the quantity of fluid retained by the sponge will be accordingly decreased due to the reduction in available pore volume. The incorporation of equal amounts of surfactant and hygroscopic agent, or of a minor amount of hygroscopic agent based on the amount of surfactant, has been found quite suitable.

Other additives, particularly germicidal and therapeutic agents such as, for example, hexachlorophene, chlortetracycline, neomycin, and penicillin can also be incorporated into the sponges.

Figure 4:
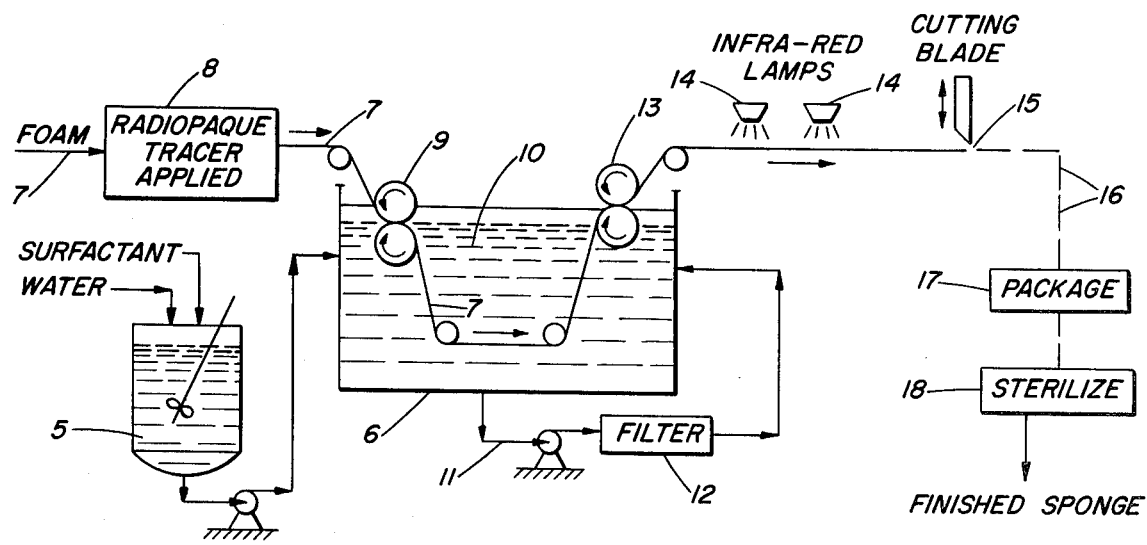
FIG. 4 is a schematic diagram illustrating a preferred method of preparing the sponges of this invention.

A preferred method for preparing the sponges of this invention is shown in FIG. 4. Referring to FIG. 4, surfactant and water are fed to mixing tank 5 where the surfactant is uniformly dispersed throughout the water. The surfactant-water dispersion is then pumped to impregnation tank 6. The radiopaque tracer is applied at 8 to a continuously advancing ribbon of polyurethane foam 7. Foam 7 advances through compression rolls 9 into impregnation bath 10 which is contained in tank 6. As foam 7 expands, bath 10 rushes into the foam pores to impregnate foam 7. Recirculating line 11 containing filter 12 is provided to remove loose pieces of foam introduced into bath 6 by the mechanical working of foam 7 by rolls 9. These loose particles must be removed to prevent their appearance in the final product. Immediately prior to emerging from bath 10, foam 7 passes through compression rolls 13 wherein a portion of impregnant is squeezed out of foam 7. Foam 7 then emerges from bath 10 and tank 6 prior to any substantial expansion thereof and passes under infrared lamps 14 whereby water is vaporized and removed from foam 7. The dry sponge is then cut by cutting blade 15 into the desired size. Sponge pieces 16 are then packaged 17 and sterilized 18.

The amount of surfactant in the final product can be controlled in several ways. The concentration of bath 10 may be fixed to insure impregnation of the required amount of surfactant into the pores of foam 7, in which case foam 7 would be-pass rolls 13, proceeding directly to lamps 14 where water would be vaporized and removed. On the other hand, bath 10 may contain a higher surfactant concentration in which case foam 7 passes through rolls 13 which are preset at an experimentally determined setting whereby excessive impregnant is squeezed from foam 7 prior to removal of water by lamps 14. The latter method is preferred since less water must be evaporated with consequent savings in manufacturing costs.

Bath 10 should not contain more than about 10% surfactant in order to avoid imparting a greasy surface to foam 7. When it is desired to add a hygroscopic agent to the foam, the agent can be conveniently added to mixing tank 5 along with water and surfactant to produce a uniform impregnation bath. A preferred impregnation bath composition is 95.5% water, 3% surfactant, and 1.5% hygroscopic agent. When a hygroscopic agent is not desired, the composition of the above bath becomes 3% surfactant and 97% water. Foam impregnation is preferably performed with bath 10 at room temperature.

The sponges are conveniently marketed in conventional dual envelope packages wherein an inner envelope containing one or more sponges is contained in an outer strippable envelope. An illustrative package of this type is described in U.S. Pat. No. 2,949,181. Alternatively, the sponges can be wrapped in one or more layers of tissue paper which would then be packaged in a strippable outer envelope. Up to 8–10 pound tissue paper is satisfactory. A suitable outer envelope is a peelable bleached microporous kraft paper (up to 30 pounds) zone coated with a cold sealable adhesive.

The packaged sponges can be sterilized using conventional methods such as heat sterilization, X-rays, beta or gamma radiation, or various liquid and gaseous chemical sterilants. A preferred method of sterilization is by gaseous ethylene oxide. For example, the packaged sponges are sterilized by placing them in an oven, evacuating the oven under 15 inch vacuum for 30 minutes and then filling the oven with a mixture of 20% ethylene oxide and 80% carbon dioxide vapor for 18 hours at an oven temperature of 124°F., a pressure of 40 psia, and 50–65% relative humidity (steam charged to oven separately); the oven is then evacuated for 90 minutes, after which the over pressure is raised to atmospheric pressure by the admittance of carbon dioxide. Sterile packaged sponges are then removed from the oven.

Figure 5:
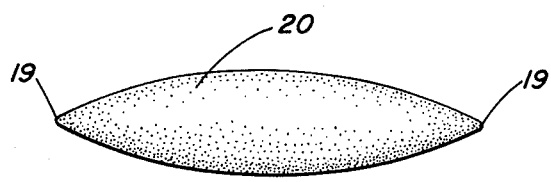
FIGS. 5 and 6 illustrate sponge configurations which are particularly suitable for use in ophthalmic surgery.

The sponge of this invention may be cut, shaped or otherwise fabricated into various configurations suitable for a host of applications. FIG. 5 shows a sponge of suppository configuration having two slightly rounded narrow ends 19 and a relatively thick central portion 20 for grasping with the hand. Points 19, due to their small size, can be readily inserted into the eye during ophthalmic surgery to remove fluids therefrom.

Figure 6:
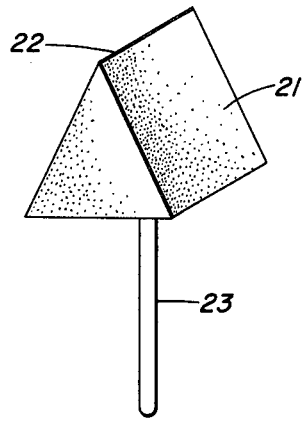

FIG. 6 shows another embodiment of a sponge useful in ophthalmic surgery. The sponge 21 is in the shape of a triangular wedge having a fine point 22, which can be inserted into the eye. Sponge 21 is mounted on shaft 23 which is provided for ease of handling.

Figure 7:
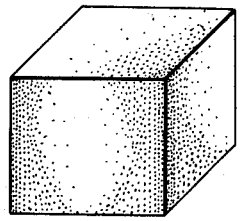
FIG. 7 is a cubed configuration of the sponge of this invention which finds general utility in surgery.

FIG. 7 is a sponge cube useful in general surgery and in a variety of other medical applications such as surgical prepping, swabbing, sponging, etc.

Figure 8:
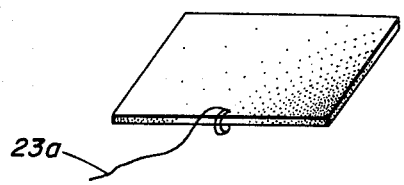
FIGS. 8 and 9 illustrate configurations of the sponge of this invention which are particularly useful in neurosurgery.
Figure 9:
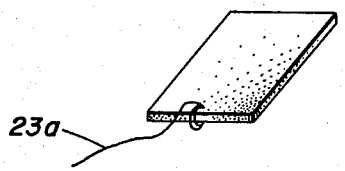

FIGS. 8 and 9 illustrate sponges particularly suitable for use in neurosurgery. These sponges are typically offered in smaller sizes ranging anywhere from as small as ½ × ½ inch to as large as 3 × 3 inch. Attached to each sponge is thread 23a which, in view of the relatively small size of these sponges, is provided for easy removal of the sponges from the operating field. Thread 23a ordinarily contains a radiopaque tracer material as a precaution.

Other sponge configurations and embodiments designed in accordance with particular medical and surgical applications also fall within the scope of this invention although not shown in this specification. For example, the sponges with a proper impervious backing can be used as a catamenial bandage or napkin to absorb menstrual fluid, or as a catamenial tampon for insertion into the vaginal cavity for a similar purpose. The sponges of this invention may also be used as aerated bandages or wound dressings. To be useful in such as application, the sponge surface in contact with the wound should not stick to the wound when the bandage is removed. Small amounts of a release agent or a nonsticking agent may be applied to the bandage surface for this purpose. Cosmetic grade silicones are effective release agents for this purpose. Other additives such as germicides and therapeutic agents may also be incorporated into such bandages.

Figure 10:
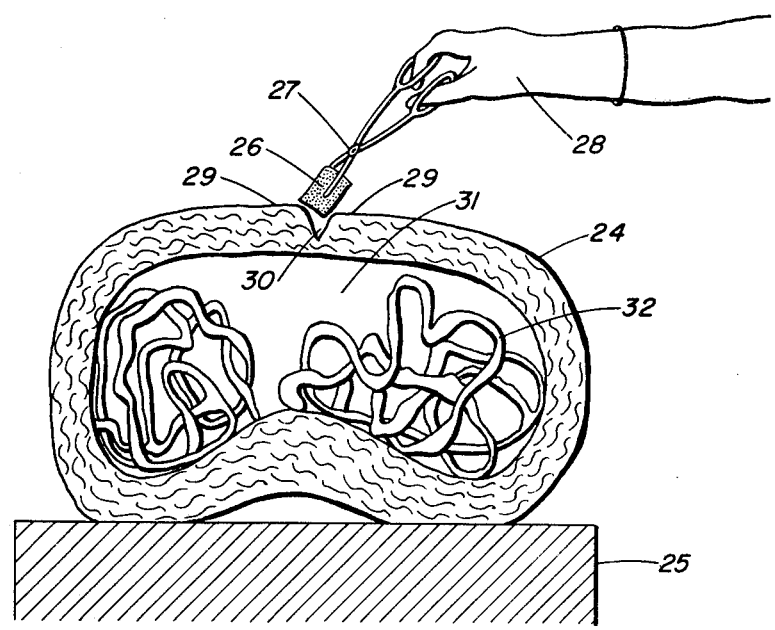
FIG. 10 is a frontal sectional view of a patient on an operating table and illustrates usage of the sponge of this invention for the removal of body fluids during an initial surgical incision.

FIG. 10 is a front sectional view of a patient 24 lying on operating table 25 and illustrates use of the sponges of this invention to remove blood and other body fluids during a surgical incision. Sponge 26 is grasped with forceps 27 by the surgeon 28 or other operating room personnel and applied to the external body surfaces 29 immediately adjacent to incision 30. Sponge 26 is also inserted into incision 30 to provide a clear cutting field for the surgeon as he continues incision 30 until he gains entry into body cavity 31.

Figure 11:
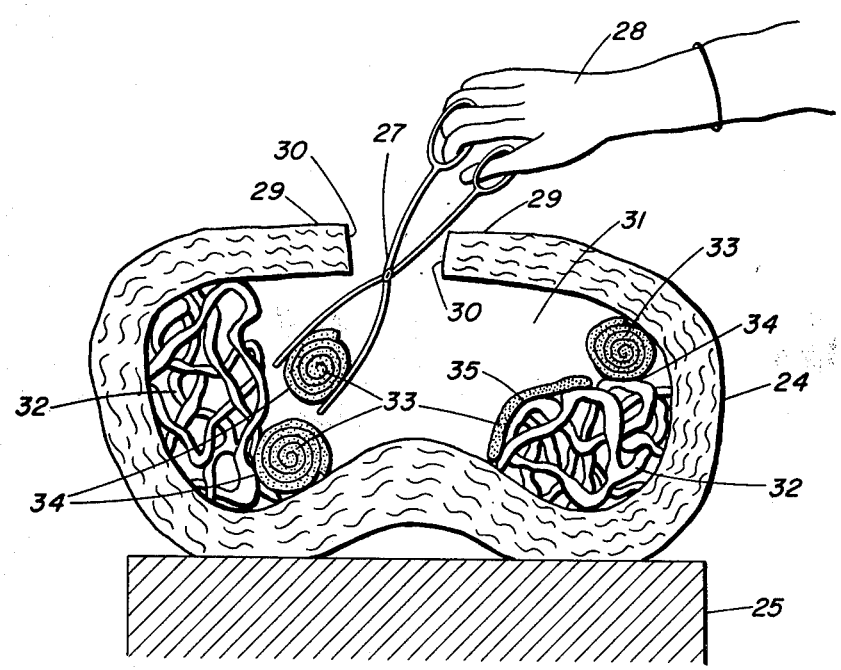
FIG. 11 is a frontal sectional view of a patient on an operating table and illustrates usage of the sponge of this invention for packing internal organs in the body cavity during surgery for purposes of maintaining a clear surgical field.

FIG. 11 illustrates the use of the sponges of this invention within body cavity 31. Once the surgeon has gained entry into cavity 31 it is necessary to push aside internal organs 32 which cover the diseased organ. To insure that organs 32 remain out of the operative field and do not interfere with the surgery, sponges 33 are inserted into cavity 31 and packed against organs 32 to retain them in the desired position. Organs 32 may be conveniently packed either by rolling a sponge into a cylindrical configuration such as is shown at 34 or by placing the sponges directly over organs 32 without rolling or otherwise altering their configuration as shown at 35.

Prior to inserting sponges in the body cavity, the dry sponges are usually placed in a basin containing saline solution and it is desirable for the sponges to be sufficiently hydrophilic to sink immediately. Untreated polyurethane foam floats for days on the surface of such solutions; however the treated polyurethane sponges of this invention sink rapidly into the solution (see Example 3 hereinbelow). Immediately before insertion of the sponge into the body cavity, the sponge is removed from the saline solution and squeezed to remove most of the liquid. It is then inserted in the body cavity as described hereinabove. The presence of some saline solution in the sponge minimizes drying out of tissue with which the sponge comes into contact. On the other hand, the sponge retains sufficient porosity to serve as a reservoir for blood and other free flowing fluids within the body cavity which could otherwise cascade into the operating field to obscure it.

The following examples are provided to further illustrate the invention.

EXAMPLE 1

RATE OF BLOOD ABSORPTION AND QUANTITY OF BLOOD RETAINED BY THE NOVEL SPONGES

TABLE I

| SPONGE IMPREGNANT | SPONGE NUMBER | SECONDS TO ABSORB ONE DROP OF BLOOD | | | | | GRAMS OF BLOOD RETAINED PER GRAM OF DRY SPONGE |
|---|---|---|---|---|---|---|---|
| 5 to 8.5% Tween-80<br><br>5 to 8.5% Glycerine | 1 | 8 | 16 | 22 | 3 | — | 18 |
| | 2 | 8 | 12 | 5 | 10 | — | 29 |
| | 3 | 4 | 6 | 5 | 5 | — | 27 |
| | 4 | 11 | 16 | 17 | 7 | — | 28 |
| | 5 | 15 | 11 | 14 | 25 | 4 | 24 |
| | 6 | 9 | 12 | 16 | 12 | 4 | 20 |
| | 7 | 12 | 6 | 10 | 60 | — | 22 |
| | 8 | 14 | 21 | 60 | 18 | — | 23 |
| | 9 | — | — | — | — | — | 24 |
| | 10 | — | — | — | — | — | 25 |
| | | AVERAGE VALUE: 14 SECONDS | | | | | AVERAGE VALUE: 24 GRAMS |
| 10.5 to 13.5% Tween-80<br><br>10.5 to 13.5% Glycerine | 1 | 4 | 6 | 3 | 12 | 5 | 22 |
| | 2 | 12 | 5 | 12 | 15 | 5 | 23 |
| | 3 | 3 | 3 | 4 | 2 | 3 | 23 |
| | 4 | 3 | 4 | 3 | 5 | 6 | 23 |
| | 5 | 5 | 3 | 4 | 3 | 3 | 16 |
| | 6 | 2 | 3 | 3 | 2 | 3 | 21 |
| | 7 | 6 | 3 | 3 | 3 | 2 | 26 |
| | 8 | 8 | 3 | 2 | 2 | 3 | 29 |
| | 9 | 22 | 2 | 4 | 7 | 3 | 24 |
| | 10 | 4 | 6 | 4 | 10 | — | 27 |
| | | AVERAGE VALUE: 5 SECONDS | | | | | AVERAGE VALUE: 23.3 GRAMS |
| 13.4 to 17.4% Tween-80<br><br>6.7 to 8.7% Glycerine | 1 | 2 | 3 | 2 | 3 | 2 | 23 |
| | 2 | 2 | 3 | 2 | 3 | 3 | 17 |
| | 3 | 4 | 3 | 3 | 2 | 3 | 12 |
| | 4 | 2 | 3 | 2 | 3 | 3 | 24 |
| | 5 | 4 | 3 | 3 | 3 | 3 | 27 |
| | 6 | 2 | 3 | 3 | 3 | 2 | 22 |
| | 7 | 2 | 2 | 2 | 3 | 2 | 22 |
| | 8 | 5 | 4 | 3 | 2 | 2 | 25 |
| | 9 | 5 | 3 | 7 | 3 | 3 | 15 |
| | 10 | 3 | 2 | 3 | 2 | 2 | 22 |
| | | AVERAGE VALUE: 3 SECONDS | | | | | AVERAGE VALUE: 20.9 GRAMS |

Sponges were prepared in accordance with the process described above and contained varying amounts of impregnated Tween-80 and glycerine. The rate of blood absorption was measured by placing a drop of blood on a 4 × 4 × ⅛ inch pad and measuring the time for the blood bubble to completely soak into the foam. When a drop of blood is placed on untreated polyurethane foam, it remains as a spherical bubble on the surface of the foam for about 30 minutes whereupon the blood begins to thicken and coagulate.

Blood retention of the sponges was determined by weighing a dry treated sponge, then completely wetting the sponge with blood by immersion therein, draining for 40 seconds, and then weighing to determine the amount of blood in the sponge.

Data are presented below in Table I which clearly show the rapid rate of blood absorption and high degree of blood retention demonstrated by the sponges of this invention. The relationship between surfactant concentration and the average absorption times of Table I is shown graphically in FIG. 3.

Surfactant and glycerine concentrations listed in Table I and shown in FIG. 3 were calculated by measuring the total amount of impregnant and then apportioning this amount between surfactant and glycerine based on the proportion of surfactant to glycerine in the impregnating bath used to prepare the sponges.

EXAMPLE 2

RATE OF WATER ABSORPTION OF THE NOVEL SPONGES

The hydrophilicity of the inventive sponges as indicated by rate of water absorption was demonstrated by taking four 2 × 2 inch squares of untreated polyurethane foam and foam which had been prepared in accordance with the process described hereinabove, stacking the four squares vertically and placing them on the surface of 25 ml. of water in a petri dish. A penny was placed on the top of the sponges to increase their weight. The amount of time required for complete absorption of the 25 ml. of water was measured for both treated and untreated foam. These results are summarized in Table II and clearly show the improvement in the rate of absorption resulting when the foam is treated according to the present invention. Treated sponges in Table II contain from about 0.09 to about 1.28% total impregnant, i.e. Tween-80 and glycerine, said sponges prepared using an impregnation bath containing 1.5% Tween-80, 1.5% glycerine, and 97% water.

TABLE II

| RATE OF ABSORPTION OF 25 Ml. TAP WATER | | | |
|---|---|---|---|
| Polyurethane Foam, Polyester Type, ⅛" Thick, 100 Pores Per Inch, 100% Reticulated | | Polyurethane Foam, Polyether Type, ⅛" Thick, 60–100 Pores Per Inch, 60% Reticulated | |
| Treated* | Controls** | Treated* | Controls** |
| Minutes-seconds | Minutes-seconds | Minutes-seconds | Minutes-seconds |
| 1–30 | 20 plus | 2–45 | 20 plus |
| 2–18 | 9–30 | 3–0 | 20 plus |
| 3–48 | 15 plus | 2–30 | 20 plus |

TABLE II-continued

RATE OF ABSORPTION OF 25 Ml. TAP WATER

| Polyurethane Foam, Polyester Type, ⅛" Thick, 100 Pores Per Inch, 100% Reticulated | | Polyurethane Foam, Polyether Type, ⅛" Thick, 60–100 Pores Per Inch, 60% Reticulated | |
|---|---|---|---|
| Treated* | Controls** | Treated* | Controls** |
| 2–30 | 4–45 | 2–18 | 20 plus |
| 3–0 | 12–18 | 3–30 | 20 plus |
| 2–30 | 13–16 | 2–2 | 20 plus |

*Treated — sponges impregnated with Tween-80, glycerin and water; passed through rollers and dried
**Controls — sponges used with no treatment.

EXAMPLE 3

WETTING TIME IN WATER AND QUANTITY OF WATER RETAINED BY THE NOVEL SPONGES

The quantity of water retained was measured by placing a square of both treated and untreated polyurethane foam on the surface of water. The wetting time, defined as the time required before the last corner of the square had submerged in the water, was recorded. The sample was then removed from the water, drained one minute, and weighed. The resultant data are presented in Table III and indicate that wetting time is substantially decreased with treated foam. The results further indicate that the sponges of this invention can absorb up to about 23 times their dry weight of water. Treated sponges in Table III contain from about 0.09 to about 1.28% total impregnant, i.e. Tween-80 and glycerine, said sponges prepared using an impregnation bath containing 1.5% Tween-80, 1.5% glycerine, and 97% water.

may be embossed rather than smooth to give a waffle-like or textured appearance. The operation of crushing to remove the elastic memory is called texturizing and the texturizing by embossing at high pressure without shear on the sponge gives the desired characteristics without markedly weakening the sponge. Even if the sponge is somewhat crushed, in contact with liquids it swells to its original thickens so that the liquid retention capabilities are affected minimally while the dead fold characteristics are markedly improved. This is particularly useful in placing sheets in a draped position in an internal body cavity during operations. The sponge possesses certain of the characteristics of a chamois skin, which has a remarkably limp hand but yet is tenuous and strong.

EXAMPLE 4

Figure 12:
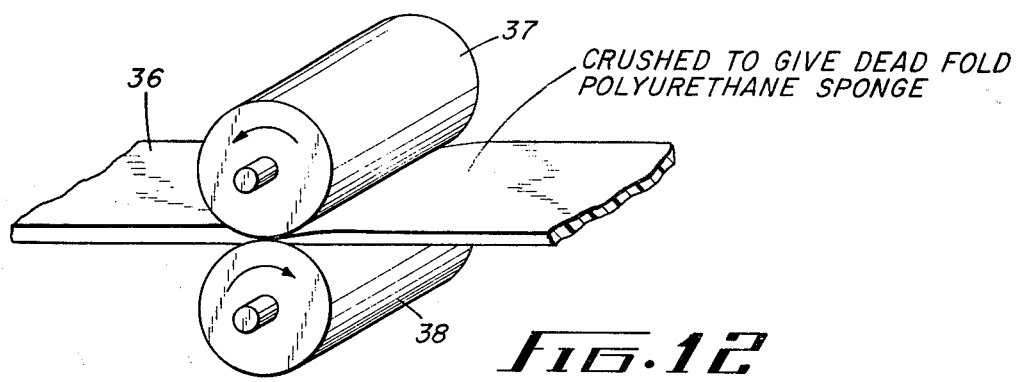
FIG. 12 shows texturizing or crushing of a polyurethane foam sheet.

As shown in FIG. 12, a sheet of hydrophilic polyurethane foam 36 which is about an ⅛ inch thick in a sheet 54 inch wide and about 100 pores per inch is passed

TABLE III

Total Water Absorption of Sponge*

| Polyurethane Foam, Polyester Type, ⅛" Thick, 100 Pores Per Inch, 100% Reticulated | | | | | Polyurethane Foam Polyether Type, ⅛" Thick, 60–100 Pores Per Inch, 60% Reticulated | | | | |
|---|---|---|---|---|---|---|---|---|---|
| Sinking Time (min.-sec.) | Weight Wet (grams) | Weight Before Sinking (grams) | Wt. Water Retained Per Sponge (grams) | Controls** | Sinking Time (min.-sec.) | Weight Wet (grams) | Weight Before Sinking (grams) | Wt. Water Retained Per Sponge (grams) | Controls** |
| 4–0 | 23.0 | 0.8 | 22.2 | | 0–45 | 19.8 | 1.0 | 18.8 | |
| 5–0 | 17.5 | 0.8 | 16.7 | | 2–1 | 19.1 | 0.9 | 18.2 | |
| 3–10 | 20.5 | 0.8 | 19.7 | Sinking Time of Controls- 100 hours or more | 0–35 | 22.1 | 0.9 | 21.2 | Sinking Time of Controls- 100 hours or more |
| 5–2 | 20.5 | 1.0 | 19.5 | | 0–42 | 19.3 | 1.0 | 18.3 | |
| 4–30 | 20.5 | 0.9 | 19.6 | | 0–46 | 20.6 | 1.0 | 19.6 | |
| 4–0 | 22.5 | 0.9 | 21.6 | | 2–1 | 20.7 | 1.0 | 19.7 | |
| 4–10 | 21.6 | 0.9 | 20.7 | | 3–10 | 21.0 | 0.9 | 20.1 | |
| 2–1 | 21.1 | 0.9 | 20.2 | | 1–55 | 20.0 | 0.9 | 19.1 | |

*Sponges impregnated with Tween-80, glycerin, and water; passed through rollers and dried.
**Used with no treatment.

In common with many plastics, polyurethane foam has an elastic memory. That is, it tends to spring back to the form in which it has previously existed. In surgical procedures at times it is desirable to drape a sheet of sponge over internal organs, and it is desired that the sheet of the sponge stay in whatever configuration or position it is placed. The characteristics of being both flexible, but also having once been placed, remaining in that position, is frequently referred to as dead fold. That is once folded, the material remains folded. It is also the opposite of elastic memory. The hydrophilic sponge of the present invention can have its elastic memory markedly reduced and tends towards dead fold characteristics if the foam is crushed between press rolls. A pressure may be used which is heavy enough to crush the sheet to a rather thin film, which then partially recovers its original thickness, or the rolls between polished steel rollers 37 and 38. 10 inch rollers are used with highly polished surfaces which are biased towards each other by air cylinders with a diameter of 6 inch and 65 pounds operating pressure of air biasing the ends of the axes to hold the cylinders together. The foam is crushed either wet or dry at speeds between 50 and 200 feet per minute. The foam regains a majority of its original thickness but has the desired dead fold characteristics. Fortunately and fortuitously the crushing appears if anything to increase the moisture retention characteristics of the foam without deleteriously effecting the strength characteristics from the standpoint of being able to pull the foam in a single piece from the wound when desired.

Figure 13:
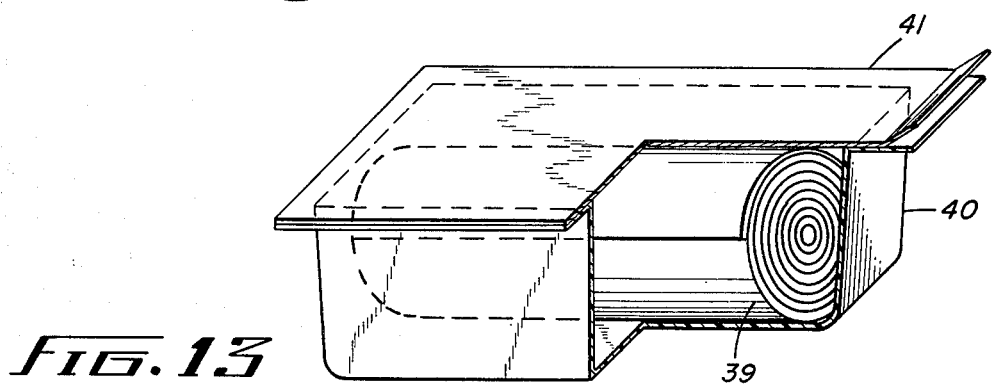
FIG. 13 shows a strippable blister package containing a polyurethane laparotomy sponge.
Figure 14:
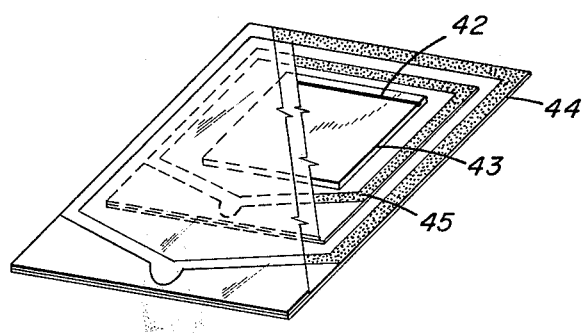
FIG. 14 shows a double strippable package with a sheet of foam.

The sheet as so texturized was rolled into rolls about 4 inch long and an inch diameter to form a roll sponge 39 as shown in FIG. 13. The roll sponges are placed in blister packages 40 with a strip sheet 41 being strippably sealed to close the package. After packaging, the assembly was treated with sterilizing doses of radiation to insure that the product was sterile.

Alternatively, the contents of the package are sterilized by using a laminate such as described in U.S. Pat. No. 2,949,181 supra, with ethylene oxide diffusing through the seal into the interior thus sterilizing the contents.

Alternatively, 2 to 30% ethylene oxide in a solvent such as ethyl alcohol, acetone or other ketone or alcohol which is volatile may be placed in the tub when the package is sealed and the solvent and ethylene oxide diffuse out of the package during storage, but before the time of use.

EXAMPLE 5

A portion of the sponge sheet from Example 4 was cut into 2 inch squares and a black polyvinyl chloride filament 42 containing approximately 60% X-ray grade barium sulfate was sealed near one edge to give an X-ray opaque. The 2 inch squares containing the heat sealed X-ray tracer were packaged in a double strippable envelope of the type disclosed in said U.S. Pat. No. 2,949,181. The outer envelope 44 may be stripped to release the sterile inner envelope containing the sponge which sponge is thus protected during handling in the operating room and yet is retained in an interior envelope 45 which may be stripped just before the sponge is to be used. Also, if because of change in requirements, the internal package may be again stored with the sponge being again strippably sterilely released at a later time. The advantages of multiple serving are disclosed in U.S. Pat No. 3,202,273, Riall.

The sponges gave good absorption when used in tests on living tissue to absorb blood.

EXAMPLE 6

Figure 15:
FIG. 15 shows a single strippable package with an internal protective sheet.

4 inch squares of ⅛ inch polyurethane form of 100 pores per inch to which a black polyvinyl barium sulfate X-ray opaque had been ultrasonically sealed, were doubled to provide a double sponge 46 as shown in FIG. 15 and the double sponges were placed in a glassine folded paper 47 which was placed in an externally sealed enveloped 48. This type of package for surgical fabrics is disclosed in U.S. Pat. No. 3,107,990, Singerman. An impregnant of 10% by weight of a 75% Tween 80, 25% glycerine mixture in water was used to coat the foam.

At time of use, the outer envelope was stripped open, and the glassine protective layer was unfolded, releasing the sponge in sterile condition. Conveniently, but not necessarily the sterile sponge is then dipped into sterile saline water, most of the sterile saline squeezed out, and the moist sponge is then placed in protective relationship with exposed raw tissue. Because of the saline water being present, the tissues do not dry and are protected during a surgical procedure.

Although particularly described in connection with a surfactant coated hydrophobic reticulated polyurethane foam, an essentially hydrophilic polyethylene foam is produced from a polyether or polyester containing hydroxy or carboxy groups which are not reacted with isocyanate groups during the manufacture of polyurethane foam are considerably more hydrophilic, and particularly when coated with glycerine as for example dipping in a 1% glycerine in water solution, using the process shown in general in FIG. 4, with the foam dried, and crushed as above described. The crushing appears to increase the water absorption characteristics.

Although described as heat sealed, multiple layers of the foam may be flame laminated or laminated to an X-ray opaque by a flame or ultrasonic sealing method. Additionally the foam may be heat or flame or ultrasonically sealed to a textile scrim. For example a thin gauze fabric of cotton or nylon gauze may be sealed to one side of the sponge to give additional rigidity. Such rigidity is useful if the sponge is to be used in holding tissues in location during an operation and additionally it permits the sponge to be used in locations where greater strength is desired for positively removing the sponge after a surgical procedure is finished.

It would unduly lengthen an already prolix specification to describe all of the multitudinous surgical uses for the present polyurethane foam sponges. The above examples are representative of the present invention, the scope of which is set forth in the following claims.

We claim:

1. A method for removing internal body fluids from surgical incisions which comprises contacting internal body fluids with a sterile hydrophilic sponge adapted for medical usage comprising a thin flexible hydrophilic polyurethane foam,
   a. the surface of said foam being non-abrasive towards internal body organs exposed during surgery,
   b. said foam containing at least one zone of intercommunicating pores extending inwardly from a surface of the foam,
   c. said pores being of sufficiently small dimension to insure retention of body fluids therein substantially by capillarity,
   d. the surface of said pore zone being substantially free from obstructions which inhibit flow of fluids into the pores,
   e. substantially all of the internal surfaces of said pores being hydrophilic and substantially non-foaming when the sponge is moistened,
   f. the polyurethane foam being crushed to possess dead fold characteristics whereby when once placed in position, the foam does not resiliently return by elastic memory to a different position, and
   g. the sponge being stored in sterile condition in a strippable package and just before use, the package is stripped open to release the sponge in sterile condition, and the sponge is then aseptically transferred to contacting relationship with raw body tissues, whereby substantial amounts of internal body fluids based on the dry weight of the sponge are absorbed by the sponge and removed from their environment upon contact of said internal fluids with said pore zone, and then removing said sponge containing said absorbed fluids from the body environment.

* * * * *